(12) United States Patent
Spulber et al.

(10) Patent No.: US 11,421,106 B2
(45) Date of Patent: Aug. 23, 2022

(54) VESICLE INCORPORATING TRANSMEMBRANE PROTEIN

(71) Applicant: AQUAPORIN A/S, Kongens Lyngby (DK)

(72) Inventors: Mariana Spulber, Nivå (DK); Dana Cristina Tvermoes, Copenhagen (DK); Radoslaw Gorecki, Copenhagen (DK); Frederick Haugsted, Copenhagen (DK)

(73) Assignee: AQUAPORIN A/S, Kongens Lyngby (DK)

( * ) Notice: Subject to any disclaimer, the term of this patent is extended or adjusted under 35 U.S.C. 154(b) by 211 days.

(21) Appl. No.: 16/755,244

(22) PCT Filed: Oct. 19, 2018

(86) PCT No.: PCT/EP2018/078730
§ 371 (c)(1),
(2) Date: Apr. 10, 2020

(87) PCT Pub. No.: WO2019/081371
PCT Pub. Date: May 2, 2019

(65) Prior Publication Data
US 2020/0239685 A1  Jul. 30, 2020

(30) Foreign Application Priority Data

Oct. 25, 2017 (DK) .............................. PA201770806
Dec. 6, 2017 (DK) .............................. PA201770915
Apr. 5, 2018 (DK) .............................. PA201870200
Aug. 29, 2018 (DK) .............................. PA201870553

(51) Int. Cl.
| | | |
|---|---|---|
| *C08L 71/02* | (2006.01) | |
| *B01D 63/04* | (2006.01) | |
| *B01D 63/10* | (2006.01) | |
| *B01D 69/08* | (2006.01) | |
| *B01D 69/12* | (2006.01) | |
| *B01D 69/14* | (2006.01) | |
| *B01D 71/60* | (2006.01) | |
| *B01D 71/80* | (2006.01) | |
| *C08G 65/08* | (2006.01) | |
| *C08L 89/00* | (2006.01) | |

(52) U.S. Cl.
CPC .............. *C08L 71/02* (2013.01); *B01D 63/04* (2013.01); *B01D 63/10* (2013.01); *B01D 69/08* (2013.01); *B01D 69/12* (2013.01); *B01D 69/144* (2013.01); *B01D 71/60* (2013.01); *B01D 71/80* (2013.01); *C08G 65/08* (2013.01); *C08L 89/00* (2013.01); *C08G 2650/58* (2013.01)

(58) Field of Classification Search
CPC ............ C08G 2650/00; C08G 2650/28; C08G 2650/58; C08L 71/00; C08L 71/02; B01D 69/144; B01D 71/60; B01D 71/80; B01D 69/141
See application file for complete search history.

(56) References Cited

FOREIGN PATENT DOCUMENTS

| | | |
|---|---|---|
| WO | 2006122566 A2 | 11/2006 |
| WO | 2007033675 A1 | 3/2007 |
| WO | 2014063097 A1 | 4/2014 |

OTHER PUBLICATIONS

Xie et al. "An aquaporin-based vesicle-embedded polymeric membrane for low energy water filtration" (J. Mater. Chem. A, 2013, 1, p. 7592-7600) (Year: 2013).*
Intellectual Property Office of Singapore, Written Opinion for Application No. 11202002669S, dated Apr. 6, 2021, 7 pages.
International Search Report; PCT/EP2018/078730; dated Mar. 19, 2019; 2 Pages (Part of International Publication WO 2019/081371 A1).

* cited by examiner

*Primary Examiner* — Ryan B Huang
(74) *Attorney, Agent, or Firm* — Ziegler IP Law Group, LLC

(57) ABSTRACT

A vesicle incorporate a transmembrane protein, the vesicle forming material including a mixture of poly(ethylene glycol)-block-poly(propylene glycol)-block-poly(ethylene glycol) and polyetheramine. The vesicle can generally withstand elevated temperature without substantial shrinkage of the diameter, which in turn results in maintenance of the water permeability virtually unaffected. Pluronic based vesicles have a large content of amino groups available on the surface illustrated by the larger zeta potential values available for crosslinking in the polyamide layer by chemical reaction with trimesoyl chloride (TMC).

20 Claims, No Drawings

VESICLE INCORPORATING TRANSMEMBRANE PROTEIN

TECHNICAL FIELD

The disclosure relates to a vesicle incorporating a transmembrane protein, a method of preparing vesicles incorporating a transmembrane protein, a separation membrane comprising a vesicle incorporating a transmembrane protein, and a method of preparing a thin film composite layer immobilizing vesicles incorporating a transmembrane protein on a porous substrate membrane.

BACKGROUND

Polymersomes or polymeric vesicles are self-assembled structures formed by amphiphilic block copolymers in a suitable solvent (eg. water), and present an inner empty cavity surrounded by a bilayered wall that can incorporate various structures, like transmembrane proteins. The stability of polymer vesicles is increasing with the molecular weight of the forming polymer and their permeability with increasing of hydrophilic to hydrophobic ratio. Block copolymers of polyoxyethylene-polyoxypropylene-polyoxyethylene (PEO-PPO-PEO), commonly known as Pluronic, with low hydrophilic to hydrophobic ratio values can form vesicles and therefore are suitable to obtain permeable membranes. Unfortunately, they are not easy to self-assemble by direct dissolution. Assembling in microfluidic devices is more suitable (Débora F. do Nascimento et al, Microfluidic Fabrication of Pluronic Vesicles with Controlled Permeability Langmuir 2016, 32, 5350-5355). Moreover, Pluronics with very high PPO/PEO ratio (eg 68/10) are known to self-assemble into vesicle structures around 100 nm, that are not very stable. Even when stabilized via a permanent interpenetrating network (IPN) of polymerized pentaerythritol tetra-acrylate (PETA) they have a shelf life not longer than one month. (Feng Li, Pluronic polymersomes stabilized by core cross-linked polymer micelles, Soft Matter, 2009, 5, 4042-4046).

Pluronics with small PPO/PEO ratio can self-assemble in the presence of anionic surfactant or inorganic salts (as sodium dodecyl sulfate or NaF) forming structures around 800 nm up to 3000 nm. (Li, F.; Ketelaar, T.; Marcelis, A. T. M.; Leermakers, F. A. M.; Stuart, M. A. C.; Sudholter, E. J. R., Stabilization of polymersome vesicles by an interpenetrating polymer network. Macromolecules 2007, 40 (2), 329-333.; Chen, S.; Yang, B.; Guo, C.; Ma, J. H.; Yang, L. R.; Liang, X. F.; Hua, C.; Liu, H. Z., Spontaneous Vesicle Formation of Poly(ethylene oxide)-Poly(propylene oxide)-Poly(ethylene oxide) Triblock Copolymer. Journal of Physical Chemistry B 2008, 112 (49), 15659-15665.).

Pluronics are considered non-toxic and are widely used in drug delivery systems and provide exciting opportunities for gene therapy. (Feng Li, Pluronic polymersomes stabilized by core cross-linked polymer micelles, Soft Matter, 2009, 5, 4042-4046). Many studies have shown the potential use of Pluronics as an adjuvant to increase both cell-mediated and antibody-mediated immune responses when used with a broad spectrum of antigens (Jain-Gupta N, et al, Pluronic P85 enhances the efficacy of outer membrane vesicles as a subunit vaccine against Brucella melitensis challenge in mice, FEMS Immunol Med Microbiol 66 (2012) 436-444).

More studies describe the ability of poloxamer to self-assemble in micelles able of including various more hydrophobic drugs and to transport them in human bodies (Yapar A E, Inal O, Poly(ethylene oxide)-Poly(propylene oxide)-Based Copolymers for Transdermal Drug Delivery: An Overview, Trop J Pharm Res, October 2012; 11 (5):855; Kamboj V K, Verma P K, Poloxamers based nanocarriers for drug delivery system, Der Pharmacia Lettre, 2015,7 (2):264-269,Batrakova E V et al, Polymer Micelles as Drug Carriers). Block copolymers including pluronics as pluronic-polylactic copolymer self-assembles in vesicles that can load and transport various cargo (eg. insulin) (Xiong X Y Vesicles from Pluronic/poly(lactic acid) block copolymers as new carriers for oral insulin delivery, Journal of Controlled Release 120 (2007) 11-17).

Pluronics can exhibit biological activity including effects on enhancing DNA cellular uptake, nuclear translocation, and gene expression. The Pluronics with a higher hydrophilic-lipophilic balance value lead to homogeneous distribution in the cytoplasm; those with a lower hydrophilic-lipophilic balance value prefer to localize in the nucleus (Fan W et al. Degradable gene delivery systems based on Pluronics-modified low-molecular-weight polyethylenimine: preparation, characterization, intracellular trafficking, and cellular distribution, International Journal of Nanomedicine 2012:7 1127-1138).

Vesicles comprising transmembrane proteins, such as aquaporins, can be used to make membranes having immobilized Aquaporins for applications such as the purification of water (WO2006/122566) or the generation of salinity power (WO2007/033675). The vesicles are generally deposited as a layer or in a film on a supporting substrate, which allows the selective passage of water molecules through the membranes by nanofiltration, reverse osmosis, forward osmosis or pressure retarded osmosis.

WO2013/043118 discloses thin film composite (TFC) membranes in which vesicles incorporating aquaporin water channels (AQPs) are immobilized. In addition, it discloses a method of producing thin film composite membranes and their uses in filtration processes, such as nanofiltration and osmotic filtration processes. WO2010/146365 describes preparation of TFC-aquaporin-Z (AqpZ) filtration membranes that use an amphiphilic triblock copolymer as a vesicle forming substance for incorporating immobilized AQPs. WO2014/108827 discloses a hollow fiber (HF) module having fibers modified with a thin film composite (TFC) layer comprising aquaporin water channels in which the aquaporin water channels may be incorporated in lipid or block copolymeric vesicles before incorporation into the TFC layer.

However, typically in the prior art, the amphiphilic lipids and block copolymers used in vesicle production are solids that need to be dissolved in harsh solvents, such as tetrachloromethane ($CCl_4$) or chloroform ($CHCl_3$), to solubilize their predominantly hydrophobic portions. In the membrane synthesis, this solvent is evaporated to allow film formation which is then rehydrated to bring the amphiphile into various emulsion forms (such as vesicles), with simultaneous incorporation of the AQP membrane protein. It would be desirable to develop a process which uses solvents having a lower environmental impact.

Industrial membranes may be treated at elevated temperatures during the separation process or the cleaning process. When the membrane is used for treatment of foodstuff such as dairy products it is generally desired to disinfect the membranes to avoid the development of microorganisms. The prior art membranes having incorporated vesicles tend to deteriorate fast when exposed to elevated temperatures. In one aspect of the present invention it is the object to develop vesicles for incorporation into membranes, which exhibit a higher temperature stability, while maintaining a suitable water permeability after a treatment at an elevated temperature.

SUMMARY

The aspects of the disclosed embodiments relate to a vesicle incorporating a transmembrane protein, wherein the vesicle membrane forming material comprises a mixture of poly(ethylene glycol)-block-poly(propylene glycol)-block-poly(ethylene glycol) and polyetheramine.

The vesicle according to the disclosed embodiments generally withstand elevated temperature without substantial shrinkage of the diameter. The low shrinkage of the vesicle diameter results in a high mechanical dimensional stability of the membrane, which in turn provides for long production life. Furthermore, the low shrinkage maintains the water permeability virtually unaffected.

The poly(ethylene glycol)-block-poly(propylene glycol)-block-poly(ethylene glycol) usually is a substantially linear polymer having a weight average molecular weight of between about 1,000 Da to about 15,000 Da, such as a weight average molecular weight of between about 2,500 Da to about 10,000 Da. In a certain aspect, the weight average molecular weight is above 3,000 Da, such as above 4,000 Da and preferably above 5,000 Da. However, usually, the weight average molecular weight of this aspect is not higher than 8,000 Da, such as not higher than 7,000 Da, and preferably not higher than 6,000 Da. In a preferred aspect the weight average molecular weight is around 5,800 Da.

The poly(ethylene glycol)-block-poly(propylene glycol)-block-poly(ethylene glycol) may have different composition and proportion of the blocks but generally the compound may be represented by the chemical formula:

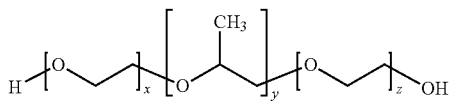

a. in which
b. x denotes an integer between 10-30
c. y denotes an integer between 50-100
d. z denotes an integer between 10-30

In a certain embodiment of the invention, x denotes an integer between 15-25, y denotes an integer between 60-80, and z denotes an integer between 15-25. In a certain implementation of the invention x and y have the same meaning. Furthermore, x and z are preferably around 20 and y is around 70. This compound is available as Pluronic P-123. In an alternative embodiment, x and z are in the range of 30-200 and y is in the range 40-60. A specific example according to this alternative embodiment is poloxamer 407 (BASF trade name: Pluronic F127), in which x=z=101 and y=56.

The polyetheramine usually contains one or more primary amino groups attached to a polyether backbone. The polyether backbone is normally based on propylene oxide (PO) or a mixture of propylene oxide (PO) and ethylene oxide (EO). When a mixture of propylene oxide (PO) and ethylene oxide (EO) is used the molar ratio PO/EO is usually higher than 1, i.e. polyetheramine is predominately polypropylene glycol (PPG) based. In a preferred aspect, the molar ratio PO/EO is usually higher than 2, such as higher than 3.

The polyether backbone may contain 1 to 3 amine groups, i.e. the polyether is a monoamine, diamine, or triamine. In a preferred aspect of the invention the polyether amine is a monoamine. When a mixture of propylene oxide (PO) and ethylene oxide (EO) is applied the amine group is predominantly positioned at the end of the propylene oxide (PO) part of the molecule.

The molecular weight of the polyetheramine generally ranges from 500 to 5000 Da. In a certain aspect of the invention, the molecular weight is from 1000 to 4000 Da, such as 1500 to 3000 Da. In a preferred aspect of the invention the molecular weight of the polyetheramine is around 2000 Da.

In a certain embodiment of the invention, the polyetheramine is of the general structure

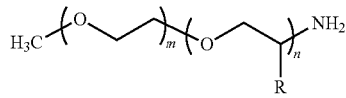

in which
m is an integer of 1-15
n is an integer of 5-50
R is $CH_3$.

In a certain aspect of the invention the ratio n/m is 1 or more, such as 2 or 3 or more. More suitable, m designates an integer of 2 to 10, such as 4-8. Most preferred around 6. n is suitably in the range of 10 to 40, such as in the range of 25 to 35.

The proportion between the poly(ethylene glycol)-block-poly(propylene glycol)-block-poly(ethylene glycol) and the polyetheramine may be selected with in broad ranges. Usually, however, the proportion by weight between the poly(ethylene glycol)-block-poly(propylene glycol)-block-poly(ethylene glycol) and the polyetheramine is 5 to 1.

It is presently believed that the poly(ethylene glycol)-block-poly(propylene glycol)-block-poly(ethylene glycol) forms the backbone of the vesicle, in which the propylene glycol units assemble into a hydrophobic domain and the ethylene glycol protrudes into the extravesicular space. The hydrophobic part of the polyetheramine will anchor the molecule in the vesicle, resulting in the amine groups to be protruding into the extravesicular space. Thus, the polyetheramine may be said to decorate the surface of the vesicles with amine groups.

Transmembrane proteins span in their natural environment the entire bilipid membrane, i.e. from the interior of the cell to the extracellular space. Many of the transmembrane proteins functions as gateways for specific substances, thereby allowing exchange of these substances between the interior of the cell and the extracellular liquid. A characteristic feature of transmembrane proteins is the presence of a hydrophobic area, which will ensure integration of the transmembrane protein into the membrane. The transmembrane protein furthermore has hydrophilic segments on both sides of the hollow fiber area, said hydrophilic segments being directed to the interior of the cell and the extracellular fluid, respectively. In the present invention, the transmembrane protein is incorporated into the hydrophobic part of the vesicles.

While any transmembrane protein may by incorporate in the membrane material disclosed in the present invention, it is generally desired to use transmembrane protein that transport ions (ion channels) and water (aquaporin water channels). Ion channels include chloride channels and metal ion transporters. Chloride channels in addition to the chloride ion also conducts $HCO_3-$, $I-$, $SCN-$, and $NO_3-$ in some transmembrane proteins. The metal ion transporters include magnesium transporters, potassium ion channels, sodium ion channels, calcium channels, proton channels etc.

In a preferred embodiment of the invention, the transmembrane protein is an aquaporin water channel. Aquaporin water channels facilitate the transport of water in or out of a cell. In an industrial membrane, the aquaporin water channels ensure the flow of water by osmosis, while others salutes in the solution are rejected.

Transmembrane proteins tend to aggregate and precipitate in aqueous solutions and it may therefore be suitable that the transmembrane protein is solubilized in a detergent. While a number of detergent may be used, generally the detergent is selected from the group consisting of lauryldimethylamine N-oxide (LDAO), octyl glucoside (OG), dodecyl maltoside (DDM) or combinations thereof.

The invention also relates to a method of preparing vesicles incorporating a transmembrane protein comprising the steps of
a. mixing an aqueous solution of transmembrane protein and polyetheramine,
b. adding poly(ethylene glycol)-block-poly(propylene glycol)-block-poly-(ethylene glycol) as an aqueous solution to the mixture prepared step a,
c. agitating the solution obtained in step b.

The vesicles prepared may also be referred to as polymersomes or polymeric vesicles. The vesicles are self-assembled structures formed by amphiphilic block copolymers in a suitable solvent (eg. water) during the agitation step. The vesicles present an inner empty cavity surrounded by a bilayered wall that can incorporate various structures, like transmembrane proteins.

The stability of polymer vesicles is increasing with the molecular weight of the forming polymer. Therefore, the average molecular weight of the poly(ethylene glycol)-block-poly(propylene glycol)-block-poly(ethylene glycol) is at least 1000 Dalton. However, a too high molecular weight tends to be difficult to assemble into a vesicle. Thus, the average molecular weight of the poly(ethylene glycol)-block-poly(propylene glycol)-block-poly(ethylene glycol) is preferably not above 15,000 Dalton. In a preferred embodiment of the invention the poly(ethylene glycol)-block-poly (propylene glycol)-block-poly(ethylene glycol) is a substantially linear polymer having a weight average molecular weight of between about 2,500 Da to about 10,000 Da. In an alternative embodiment of the invention, the poly(ethylene glycol)-block-poly(propylene glycol)-block-poly(ethylene glycol) has a molecular weight of 10,000 to 15,000 Da.

The permeability of the vesicle generally increases with increasing hydrophilic to hydrophobic ratio. Thus, the amount of propylene glycol units is generally higher than the amount of ethylene glycol units. Block copolymers of polyoxyethylene-polyoxypropylene-polyoxyethylene (PEO-PPO-PEO), commonly known as Pluronic, have low hydrophilic to hydrophobic ratio values and therefor are suitable to obtain permeable membranes. In an embodiment of the invention the poly(ethylene glycol)-block-poly(propylene glycol)-block-poly(ethylene glycol) has the chemical formula:

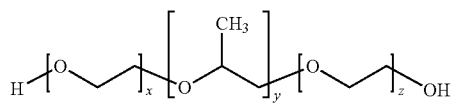

in which
x denotes an integer between 10-30, preferably 15-25;
y denotes an integer between 50-100, preferably 60-80; and
z denotes an integer between 10-30, preferably 15-25.

The polyetheramine is suitably of the general structure

in which
m is an integer of 1-15
n is an integer of 5-50
R=$CH_3$.

In an embodiment of the invention, the proportion by weight between the poly(ethylene glycol)-block-poly(propylene glycol)-block-poly(ethylene glycol) and the polyetheramine is 5 to 1.

Before the aqueous transmembrane protein, such as aquaporin, is mixed with the polyetheramine in step a, suitably the transmembrane protein is solubilized in a detergent. The solubilization of the transmembrane protein in a detergent prevent or ameliorate the tendency of the transmembrane to precipitate in the aqueous solution. Suitably, the detergent is selected from the group consisting of lauryldimethylamine N-oxide (LDAO), octyl glucoside (OG), dodecyl maltoside (DDM) or combinations thereof.

In an embodiment of the invention, the vesicles produced as disclosed above is included in a separation membrane. In on embodiment, the separation membrane comprises an active layer incorporating the vesicle and a porous support membrane. The porous support membrane should not substantially impede the flux of water and/or the ion transported by the transmembrane protein. The main purpose of the porous support membrane is to serve as a scaffold for the active layer incorporating the vesicles, thus allowing the transmembrane protein to be the predominate discriminating element.

In a preferred aspect of the invention, the active layer comprises the vesicle incorporated in a thin film composite layer formed on a porous substrate membrane. Without wishing to be bound by any particular theory, it is believed that the vesicles containing amine groups on the surface will be not only physically incorporated or immobilized in (adsorbed), but, in addition, chemically bound in the TFC layer, because the reactive amine groups, will participate in the interfacial polymerization reaction with the acyl chloride, such as a trimesoyl chloride (TMC). In this way, it is believed that vesicles will be covalently bound in the TFC layer, leading to relatively higher vesicle loading and thus higher water flux through the membranes. In addition, it is believed that the covalent coupling of vesicles in the TFC layer results in higher stability and/or longevity of the aquaporins and aquaporin-incorporated vesicles when incorporated in the selective membrane layer.

Furthermore, when said transmembrane protein comprises an ion channel or an aquaporin or the like, and said vesicles comprising said transmembrane protein are immobilized or incorporated in said active or selective layer, it becomes feasible to manufacture separation membranes or filtration membranes having diverse selectivity and transport properties, e.g. ion exchange membranes when said transmembrane protein is an ion channel, or water filtration membranes when said transmembrane protein is an aquaporin. Because the transmembrane protein maintains its biologically active folded structure when complexed into the self-assembled vesicles wherein it may be shielded from degradation. Even sensitive amphiphilic proteins may become sufficiently stable and, thus, preserve their desired functionality when processed into separation membranes in lab and industrial scale.

The aspects of the disclosed embodiments further relate to a method of preparing a thin film composite layer immobilizing vesicles incorporating a transmembrane protein on a porous substrate membrane, comprising the steps of a. Providing an aqueous solution comprising the vesicles prepared as mentioned above and a di-amine or tri-amine compound,
b. Covering the surface of a porous support membrane with the aqueous solution of step a,
c. Applying a hydrophobic solution comprising an acyl halide compound, and
d. Allowing the aqueous solution and the hydrophobic solution to perform an interfacial polymerization reaction to form the thin film composite layer.

The di-amine compound may be selected among a range of compounds including for example, phenylenediamines, such as m-phenylenediamine, p-phenylenediamine, 2,5-dichloro-p-phenylenediamine, 2,5-dibromo-p-phenylenediamine, 2,4,6-trichloro-m-phenylenediamine, 2,4,6-tribromo-m-phenylenediamine, etc; diaminobiphenyls, such as 2,2'-diaminobiphenyl, 4,4'-diaminobiphenyl, 3,3'-dichloro-4,4'-diaminobiphenyl, 3,5,3',5'-tetrabromo-4,4'-diaminobiphenyl, etc; diaminodiphenylmethanes, such as 4,4'-diaminodiphenyl-methane, 3,3'-diaminodiphenylmethane, 2,2'-diaminodiphenylmethane, 3,3'-dichloro-4,4'-diaminodiphenylmethane, 2,2'-dichloro-4,4'-diaminodiphenylmethane, 3,5,3',5'-tetrachloro-4,4'-diaminodiphenylmethane, 3,5,3',5'-tetrabromo-4,4'-diaminodiphenylmethane, etc.; diaminobibenzyls, such as 4,4'-diaminobibenzyl, 3,5,3',5'-tetrabromo-4,4'-diaminobibenzyl, etc.; 2,2-bisaminophenylpropanes, such as 2,2-bis(4'-aminophenyl)propane, 2,2-bis(3',5'-dichloro-4'-aminophenyl)propane, 2,2-bis(3',5'-dibromo-4'-aminophenyl)propane, etc.; diaminodiphenylsulfones, such as 4,4'-diaminodiphenylsulfone, 3,5,3',5'-tetrachloro-4,4'-diaminodiphenylsulfone, 3,5,3',5'-tetrabromo-4,4'-diaminodiphenylsulfone, etc.; diaminobenzophenones, such as 4,4'-diamino-benzophenone, 2,2'-diaminobenzophenone, 3,3'-dichloro-4,4'-diaminobenzophenone, 3,5,3',5'-tetrabromo-4,4'-diaminobenzophenone, 3,5,3',5'-tetrachloro-4,4'-diaminobenzophenone, etc.; diaminodiphenyl ethers, such as 3,3'-diaminodiphenyl ether, 4,4'-diaminodiphenyl ether, 3,3'-dibromo-4,4'-diaminodiphenyl ether, etc. piperazine, N-phenyl-benzene-1,3 diamine, melanine, and mixtures of such compounds. In a preferred aspect the diamine is selected as m-phenylenediamine (MPD) also known as 1,3-diaminobenzene.

The tri-amine compound may be selected among a range of compounds including for example, diethylene triamine, dipropylene triamine, phenylenetriamine, bis(hexamethylene)triamine, bis(hexamethylene)triamine, bis(3-aminopropyl)amine, hexamethylenediamine, N-tallowalkyl dipropylene, 1,3,5-triazine-2,4,6-triamine, and mixtures of these compounds.

The acyl halide compound usually has two or three acyl halide groups available for reaction with the di- or triamine compound. Suitable examples of diacyl halide or triacyl halide compounds include trimesoyl chloride (TMC), trimesoyl bromide, isophthaloyl chloride (IPC), isophthaloyl bromide, terephthaloyl chloride (TPC), terephthaloyl bromide, adipoyl chloride, cyanuric chloride and mixtures of these compounds.

The amine groups of the di-amine or tri-amine compound will compete with the acid chloride groups of the acyl halide compound for reaction. Generally, the proportion by weight of the di-amine or tri-amine compound to acyl halide compound is from 0:1 to 30:1. When a high density of vesicles on the surface is required the amount of di-amine or tri-amine groups is usually in the lower part of the range, i.e. 0:1 to 1:1, such as between 0:1 to 0.5:1. In other embodiments of the invention, a more rigid TFC layer is desired and a selection of the reactants are in the higher end of the range, such as 1:1 to 30:1, preferably 1:1 to 5:1.

The aqueous amine solution may be added to the porous support membrane in an even layer and subsequently dried before the application of the acyl halide solution. In a certain embodiment of the invention the aqueous amine solution is applied to the porous support membrane and subsequently a vacuum is provided on the opposing side of the porous support membrane to stimulate the permeation of the aqueous amine solution into the porous structure. After relief of the vacuum, the acyl chloride solution is applied for the formation of the thin film composite layer by the reaction of the amine with the acyl chloride. The use of a vacuum is believed to provide for a better integration of the thin film composite layer in the porous support membrane.

The porous support membrane may be formed by a number of materials. The specific choice of material is not essential as long as the support membrane is able sufficiently to support the TFC layer and to withstand decomposition during operation condition, i.e. able to withstand the pressure and/or the chemical environment on either side of the membrane. Specific examples of materials for the porous support membrane include polysulfone or a polyethersulfone polymer. The support may be symmetrical or asymmetrical. In the case the porous support membrane is asymmetrical, the TFC layer is suitably formed on the skin layer face.

The porous support membrane may further be supported by a woven or non-woven mechanical support in some embodiments to increase the mechanical construction and reduce the risk of fractures during operation.

The porous support membrane may any physical appearance known in the art, such as flat sheet membrane, tubular membrane, or hollow fiber membrane. In a certain aspect of the invention a hollow fiber membrane is preferred as it provides for higher packing density, i.e. the active membrane area is higher for a certain volume. The membranes may be grouped together or assembled into a module as known in the art. Thus, a plurality of flat sheet membranes may be assembled into a plate-and-frame membrane configuration. Plate-and-frame membrane systems utilize membranes laid on top of a plate-like structure, which in turn is held together by a frame-like support.

Flat sheet membranes may also be assembled into spiral-wound filter modules. In addition to the flat sheet membranes, the spiral-wound membrane modules include feed spacers, and permeate spacers wrapped around a hollow tube called the permeate tube. Spiral wound elements utilize cross flow technology, and because of its construction, can easily be created in different configurations with varying length, diameter, and membrane material. A spiral-wound filter module may be produced by first laying out a membrane and then fold it in half with the membrane facing inward. Feed spacer is then put in between the folded membranes, forming a membrane sandwich. The purpose of the feed spacer is to provide space for water to flow between the membrane surfaces, and to allow for uniform flow between the membrane leaves. Next, the permeate spacer is attached to the permeate tube, and the membrane sandwich prepared earlier is attached to the permeate spacer using glue. The next permeate layer is laid down and sealed with glue, and the whole process is repeated until all of the required permeate spacers have been attached to the membranes. The finished membrane layers then are wrapped around the tube creating the spiral shape.

Tubular membrane modules are tube-like structures with porous walls. Tubular modules work through tangential cross-flow and are generally used to process difficult feed streams such as those with high dissolved solids, high suspended solids, and/or oil, grease, or fats. Tubular modules consist of a minimum of two tubes; the inner tube, called the membrane tube, and the outer tube, which is the shell. The feed stream goes across the length of the membrane tube and is filtered out into the outer shell while concentrate collects at the opposite end of the membrane tube.

The hollow fiber membranes may be assembled into a module. Thus, the present invention provides the step of producing a hollow fiber module by assembling a bundle of hollow fibers in a housing, wherein an inlet for passing a first solution is connected to the lumen of the hollow fibers in one end and an outlet is connected to the lumen in the other end, and an inlet is provided in the housing for passing a second solution to an outlet connected to the housing.

The membrane modules produced in accordance with the present invention may be used in various configurations, including forward osmosis configurations and reverse osmosis configurations.

The aspects of the disclosed embodiments also relate to vesicles comprising an internal cargo, wherein the charged vesicles are capable of releasing the internal cargo upon pH change in the environment. The vesicles comprising a mixture of poly(ethylene glycol)-block-poly(propylene glycol)-block-poly(ethylene glycol) and polyetheramine are stable at stable at alkaline pH values, such as below pH 7 or pH 8 or above. However, when the environment external of the vesicles changes to acid values, such as pH values of pH 7 or below or pH 6 or below, the vesicle formation dissociates. The pH selective behavior of the vesicles offers the opportunity for incorporating cargo in the vesicles at alkaline pH values, transporting the vesicles with cargo to a desired location and releasing the cargo by subjecting the vesicles to acid conditions, which will allow the vesicles to dissociate.

The vesicles for cargo delivery have the same composition and preparation method as described above for vesicles incorporation transmembrane proteins. Due to the preparation method, the vesicles are very at alkaline pH values, i.e. pH from pH 7 to pH 14 and temperature from 30 to 90° C. Initial tests suggest that the vesicles are stable for at least one year at room temperature without any change.

Moreover, the vesicles reassemble at neutral or basic pHs making easy the incorporation of internal cargo when needed without any additional purification steps.

The vesicles comprising a cargo substance may be used as a carrier system for the in situ or in vivo delivery of various cargo substances, including bioactive moieties. The cargo substance may be a bioactive substance, for example, such as a bioactive substance selected from the group consisting of small molecule drugs, biomolecules, biomacromolecules and cells. The bioactive substance may be supported on a non- bioactive carrier. The cargo substance may be a polymeric or inorganic particle. Illustrative examples of substances that may be utilized as cargo substances in accordance with the present invention include, but are limited to, the following: small molecule drugs, biomolecules, biomacromolecules (including, but not limited to, polysaccharides, glycosaminoglycans, and proteins), cells (including live cells), therapeutic agents (i.e., agents that cause a measurable physiological response in an animal, such as a human), fluorophores, chromagenic agents, enzymes, proteins (including immunomodulatory proteins and matrix metalloproteinases), antibiotics, anesthetics, antibodies, growth factors, hormones, anti-inflammatories, analgesics, cardiac agents, psychotropics, fillers (e.g., inorganic and/or polymeric particles), immunotherapeutics, cytokines, oligonucleotides, labels (e.g., fluorophores, radionucleotides, fluorescent moieties, chemiluminescent moieties, magnetic particles, dyes) and the like and combinations thereof.

DETAILED DESCRIPTION OF THE EMBODIMENTS

Broadly, the aspects of the disclosed embodiments relate to the use of a mixture of poly(ethylene glycol)-block-poly(propylene glycol)-block-poly(ethylene glycol) and polyetheramine, to form self-assembled vesicles with transmembrane proteins, such as aquaporin water channels. The vesicles having incorporated the transmembrane protein may then be used in the production of separation membranes in which the transmembrane proteins are incorporated or immobilized, for example for allowing water molecules to pass through the membrane. For example, for the production of separation membranes comprising the transmembrane proteins, the vesicles may be added to an aqueous liquid composition comprising an aromatic amine, such as a diamine or triamine, e.g. 1,3-diaminobenzene (MPD) applied to the surface of a porous support structure, which when brought into contact with a solution of an acid chloride in an organic solvent will participate in an interfacial polymerization reaction to form a thin film composite active or selective layer on said support thus forming a separation membrane, wherein said vesicles have become immobilized or incorporated.

Without wishing to be bound by any particular theory, it is believed that the vesicles containing free available $NH_2$ reactive groups on the surface will be not only physically incorporated or immobilized in (adsorbed), but, in addition, chemically bound in the TFC layer, because the $NH_2$ reactive groups, will participate in the interfacial polymerization reaction with the acyl chloride, such as a trimesoyl chloride (TMC). In this way, it is believed that vesicles will be covalently bound in the TFC layer. Furthermore, it is believed that by proper adjustment of the reactive components, a high vesicle loading can be obtained and thus higher flux through a certain area of the membrane. In addition, it is believed that the covalent coupling of vesicles in the TFC layer results in higher stability and/or longevity of the vesicles comprising the transmembrane proteins when incorporated in the selective membrane layer.

Furthermore, when said transmembrane protein comprises an ion channel or an aquaporin or the like, and said vesicles comprising said transmembrane protein are immobilized or incorporated in said active or selective layer, it becomes feasible to manufacture novel separation membranes or filtration membranes having diverse selectivity and transport properties, e.g. ion exchange membranes when said transmembrane protein is an ion channel, or water filtration membranes when said transmembrane protein is an aquaporin. Because the transmembrane protein maintains its biologically active folded structure when complexed into the self-assembled nanostructures wherein it may be shielded from degradation, even sensitive amphiphilic proteins may become sufficiently stable and, thus, preserve their desired functionality when processed into separation membranes in lab and industrial scale.

The separation membrane of the disclosed embodiments is useful in an industrial or domestic setting for preparing a pure water filtrate, such as filtering an aqueous solution through a separation membrane in a nanofiltration process or in a reverse osmosis process. For the purposes herein the term "separation membrane" includes selectively permeable membranes and semipermeable membranes for water filtration and water separation, such as asymmetric membranes comprising a porous support membrane having a selective layer formed on one side, such as a thin crosslinked aromatic polyamide layer or film or a layer of alternately charged polyelectrolytes (L-B-L). The other side may be reinforced by a woven or non-woven layer or mesh typically made of polyester fibers.

In addition, the separation membrane of the disclosed embodiments is useful in a method for the concentration of a product solution, said method comprising utilizing a separation membrane of the disclosed embodiments mounted in a filter housing or module to extract water from the product solution, e.g. by forward osmosis.

In an aspect of the disclosed embodiments it includes a hollow fiber (HF) module having a bundle of hollow fiber membranes modified with a selective layer comprising the vesicle formulation of the disclosed embodiments. Preferably, the selective layer comprises a thin film composite (TFC) layer formed on the inside surface of the fibers through an interfacial polymerization reaction, wherein said TFC layer comprises aquaporin water channels incorporated in vesicles composed of a mixture of poly(ethylene glycol)-block-poly(propylene glycol)-block-poly-(ethylene glycol) and polyetheramine.

The separation membrane of the disclosed embodiments may additionally be useful in a method for the production of salinity power using pressure retarded osmosis, said method comprising utilizing said separation membrane to increase hydrostatic pressure, and using the increase in hydrostatic pressure as a source of salinity power, cf. WO2007/033675 and WO2014128293 (A1).

The term "aquaporin water channel" as used herein includes a functional natural or synthetic aquaporin or aquaglyceroporin water channel, such as aquaporin Z (AqpZ), GlPf, SoPIP2;1, aquaporin 1 and/or aquaporin 2. Aquaporin water channels include bacterial aquaporins and eukaryotic aquaporins, such as yeast aquaporins, plant aquaporins and mammalian aquaporins, as well as related channel proteins, such as aquaglyceroporins. Examples of aquaporins and aquaglyceroporins include: prokaryotic aquaporins such as AqpZ; mammalian aquaporins, such as Aqp1 and Aqp2; plant aquaporins, such as plasma intrinsic proteins (PIP), tonoplast intrinsic proteins (TIP), nodulin intrinsic proteins (NIP) and small intrinsic proteins (SIP), e.g. SoPIP2;1, PttPIP2;5 and PtPIP2;2; yeast aquaporins, such as AQY1 and AQY2; and aquaglyceroporins, such as GlpF and Yfl054. Aquaporin water channel proteins may be prepared according to the methods described herein or as set out in Karlsson et al. (FEBS Letters 537: 68-72, 2003) or as described in Jensen et al. US 2012/0080377 A1 (e.g. see Example 6).

The term "separation membrane" as used herein includes membranes useful for separating water and, optionally, certain small size solutes including anions and cations, from other solutes, particles, colloids and macromolecules. Examples of separation membranes are "filtration membranes" such as nanofiltration (NF) membranes, forward osmosis (FO) membranes and reverse osmosis (RO) membranes. One type of filtration membranes is a "thin film composite" (or TFC) membrane, often classified as nanofiltration and reverse osmosis membranes. Flat sheet TFC membranes are typically made by depositing a polyamide layer on top of a polyethersulfone or polysulfone porous layer on top of a non-woven or woven fabric support. The polyamide rejection layer is formed through interfacial polymerization of an aqueous solution of an amine with a solution of an acid chloride in an organic solvent. TFC membranes may be produced as described in WO 2013/043118 (Nanyang Technological University & Aquaporin A/S). Other types of filtration membranes are those formed by the layer-by-layer (LbL) deposition method, such as described in Gribova et al. (Chem. Mater., 24: 854-869, 2012) and Wang et al. (Membranes, 5(3): 369-384, 2015). For example, the vesicles of the invention may be embedded or incorporated in the polyelectrolyte multilayer (PEM) films, as outlined in FIG. 4 of Gribova et al.

"Thin-film-composite" or (TFC) membranes as used herein may be prepared using an amine reactant, preferably an aromatic amine, such as a diamine or triamine, e.g.,1,3-diaminobenzene (m-Phenylenediamine, >99%, e.g. as purchased from Sigma-Aldrich) in an aqueous solution, and an acyl halide reactant, such as a di- or triacid chloride, preferably an aromatic acyl halide, e.g. benzene-1,3,5-tricarbonyl chloride (CAS No. 84270-84-8, trimesoyl chloride (TMC), 98%, e.g. as purchased from Sigma-Aldrich) dissolved in an organic solvent where said reactants combine in an interfacial condensation polymerization reaction, cf. Khorshidi et al. (2016) Scientific Reports 6, Article number: 22069, and U.S. Pat. No: 4,277,344 which describes in detail the formation of a composite membrane comprising a polyamide laminated to a porous membrane support, at the surface of the support membrane, e.g. a polyethersulfone membrane. Benzene-1,3,5-tricarbonyl chloride (trimesoyl chloride) is dissolved in a solvent, such as a $C_6$-$C_{12}$ hydrocarbon including hexane (>99.9%, Fisher Chemicals), heptane, octane, nonane, decane etc. (straight chain or branched hydrocarbons) or other low aromatic hydrocarbon solvent, e.g. Isopar™ G Fluid which is produced from petroleum-based raw materials treated with hydrogen in the presence of a catalyst to produce a low odour fluid, the major components of which include isoalkanes. Isopar™ G Fluid: Chemical Name: Hydrocarbons, C10-C12, isoalkanes, <2% aromatics; CAS No: 64742-48-9, chemical name: Naphtha (petroleum), hydrotreated heavy (from ExxonMobil Chemical). Alternatives to the reactant 1,3-diaminobenzene include diamines such as hexamethylenediamine etc., and alternatives to the reactant benzene-1,3,5-tricarbonyl chloride include a adipoyl chloride, cyanuric acid etc. as known in the art.

The vesicles of the disclosed embodiments may be referred to "self-assembled" to describe the process by which vesicles are formed through hydrophilic and hydrophobic interaction of the amphiphilic substances, i.e. the mixture of poly(ethylene glycol)-block-poly(propylene glycol)-block-poly(ethylene glycol) and polyetheramine.

"Hydrodynamic diameter" as used herein represents the hydrodynamic size of nanoparticles in aqueous media measured by dynamic light scattering (DLS) defined as the size of a hypothetical hard sphere that diffuses in the same fashion as that of the particle being measured.

Forward osmosis (FO) or direct osmosis is an osmotic process that uses a selective and permeable membrane to effect separation of water from dissolved solutes. The driving force for this separation is an osmotic pressure gradient between a solution of high concentration, herein referred to as the draw and a solution of lower concentration, referred to as the feed. The osmotic pressure gradient induces a net flow of water through the membrane into the draw, thus effectively concentrating the feed. The draw solution can consist of a single or multiple simple salts or can be a substance specifically tailored for forward osmosis applications. The feed solution can be a dilute product stream, such as a beverage, a waste stream or seawater, cf. IFOA, http://forwardosmosis.biz/education/what-is-forward-osmosis/.

Most of the applications of FO, thus fall into three broad categories: product concentration, waste concentration or production of clean water as a bi-product of the concentration process. The term "PAFO" when used herein describes a pressure assisted forward osmosis process. The term "PRO" when used herein describes pressure retarded osmosis which is useful in the generation of osmotic power. Membranes of the disclosed embodiments are useful in all types of forward osmosis processes and may be specifically adapted for each forward osmosis type.

The term "reverse osmosis" (RO) as used herein refers to when an applied feed water pressure on a selectively permeable membrane is used to overcome osmotic pressure. Reverse osmosis typically removes many types of dissolved and suspended substances from feed water, including bacteria, and is used in both industrial processes and in the production of potable water. During the RO process, the solute is retained on the pressurized side of the membrane and the pure solvent, the permeate, passes to the other side. Selectivity specifies that the membrane does not allow larger molecules or ions through its pores (holes), while allowing smaller components of the solution (such as solvent molecules) to pass freely. Low pressure reverse osmosis (LPRO) membranes typically operates at a feed water pressure of from about <5 bar and up to a maximum operating pressure of about 25 bar 15 specific flux LMH/bar. LPRO performed at the lower feed pressure ranges, e.g. 2 to 5 bar is sometimes designated ultra-low pressure reverse osmosis. LPRO membranes known in the art have typical operating limits for feed water temperature of about 45° C., feed water pH in the range of 2 to 11, and chemical cleaning in the range of pH 1 to 12.

The aspects of the disclosed embodiments are further illustrated with reference to the following non-limiting examples

EXAMPLES

Example 1

Preparation of vesicles from Pluronic® P-123 triblock copolymer (poly(ethylene glycol)-block-poly(propylene glycol)-block-poly(ethylene glycol) Mn 5800 Da) and Jeffamine® M-2005 (polyetheramine) having a nominal 2000 molecular weight) and preparation of water membrane using said vesicles.

Materials:

Pluronic® P-123 triblock copolymer (poly(ethylene glycol)-block-poly(propylene glycol)-block-poly(ethylene glycol) having a composition of PEG20-PPO70-PEG20 with molecular weight of 5800 Da was purchased from Sigma Aldrich and was used as received.

Jeffamine® M-2005 is a polyetheramine with the ratio polyethylene oxide polypropylene oxide of 29 to 6 and molecular weight of 2000 Da and was purchased from Huntsman and was used as received.

Phosphate buffer 10 mM (PBS) (pH 7.2, 136 mM NaCl, 2.6 mM KCl) was prepared by dissolving 8 g NaCl, 0.2 g KCl, 1.44 g Na2HPO4 and 0.24 g of KH2PO4 in 800 mL MiliQ purified H2O, adjusting the pH to 7.2 with HCL and completing the volume to 1 L.

Aquaporin Z 5 mg/mL stock solution was prepared as disclosed below. Functional aquaporin-Z was overproduced in E. coli strain BL21(DE3) bacterial cultures as His-tagged protein with a tobacco etch virus cleavage site. The fusion protein has 264 amino acid and a Mw of 27234 Da. Genomic DNA from E. coli DH5 was used as a source for amplifying the AqpZ gene. The AqpZ gene was amplified using gene specific primers with the addition of a tobacco etch virus cleavage site (TEV); ENLYFQSN at the N-terminus of AqpZ. The amplified AqpZ was digested with the enzyme NdeI and BamHI and then ligated to the similarly digested 6-His tagged expression pET28b vector DNA. The positive clones were verified by PCR-screening. The authenticity of the constructs was then confirmed by DNA sequencing.

The E. coli strain BL21(DE3) was used for expression of the protein. Luria Broth cultures containing 50 µg/ml kanamycin were incubated for 13-16 hours at 37C, diluted 100-fold into fresh LB broth and propagated to a density of about 1.2-1.5 (OD at 600 nm). Expression of recombinant protein was induced by addition of 1 mM IPTG for 3 hour at 35° C. before centrifugation. Harvested cells were resuspended in ice-cold binding buffer (20 mM Tris pH 8.0, 50 mM NaCl, 2 mM β-mercaptoethanol, 10% glycerol) in the presence of 0.4 mg/ml lysozyme, 50 units Bensonase and 3% n-octyl β-D-Glucopyranoside. The sample was subjected to five times lysis cycles in a microfluidizer at 12,000 Pa. Insoluble material was pelleted by 30 minutes centrifugation at 40,000 × g. The supernatant was passed through a Q-Sepharose fast flow column (Amersham Pharmacia), and the flow through was 10 collected. The flow though fraction was topped up with NaCl to 300 mM before loaded onto a pre-equilibrated Ni-NTA column. The column was washed with 100 column volumes of a wash buffer (20 mM Tris pH 8.0, 300 mM NaCl, 25 mM imidazole, 2 mM β-mercaptoethanol, 10% glycerol) to remove non-specifically bound material. Ni-NTA agarose bound material was eluted with five bed volumes of elution buffer (20 mM Tris pH 8.0, 300 mM NaCl, 300 mM imidazole, 2 mM β-mercaptoethanol, 10% 15 glycerol, containing 30 mM n-octyl β-D-Glucopyranoside). AqpZ was further purified with anion exchange chromatography; monoQ column (GE healthcare). The sample mixture was diluted and concentrated to bring the salt and imidazole concentration to approximately 10 mM with Amicon concentrator, membrane cut off 10,000 Da before loading to MonoQ column. The buffer used during anion exchange chromatography were (A) 20 mM Tris pH 8.0, 30 mM OG, 10% glycerol and (B) 20 mM 20 Tris pH 8.0, 1 M NaCl, 30 mM OG, 10% glycerol. The eluted peak fractions containing AqpZ from the ion exchange column was pooled. The purified AqpZ extract was kept frozen at −80° C.

One day before the purification, the AQP extract (stored at −80° C. freezer) was thawed on ice or in a 4° C. refrigerator. Portions of the buffers and ddH2O were readied at 4° C. The AQP extract was stirred in an adequate chilled beaker on ice bath by a magnetic stick to dissolve any precipitate. 1.5 volumes of pre-chilled LDAO-free AQP binding buffer was gradually added into 1 volume of the solubilized extract (using a further 0.5 volume buffer for rinsing the extract tubes and filtration cup), mixed well and filtered through a sterile 0.45 μM vacuum filter cup. Vacuum was applied to the filter cup to avoid excess foaming and the filtrate was placed on ice to use within 2 hours.

A Histrap column was equilibrated with sterile water followed by AQP Binding buffer at RT. The flow rate was set at 1 ml/min (for 1 mL prepacked column) or 2.5 ml/min (for 5 ml prepacked column and self-packed column). The 3 times diluted extract (on ice water bath) was loaded onto the Histrap column using ÄKTA program. The flow rate was set at 1 ml/min (for 1 mL prepacked column) or 2.5 ml/min (for 5 mL prepacked column and self-packed column). The loading volume was less than 30 ml/ml resin. The extract flow-through on ice-water bath was collected and stored at 4° C. for further use. The column was washed with 10 CV (column volume) ice cold AQP binding buffer. The flow rate was set at 2.5 ml/min (for 5 ml prepacked column and self-packed column) or set at 1 ml/min for 1 ml prepacked column. The AQP protein was eluted with ice cold AQP elution buffer (10 column volume) at flow rate 2.5 ml/min using ÄKTA program. The fraction volume was set to 10 ml and collection started in 15 mL PP tubes after 0.5-1CV.

Eluted fractions were capped and stored on ice or 4° C. The AQP purity and conformation was examined by denaturing and native PAGE analysis respectively. Protein concentration was measured by Nanodrop. The extract flow-through may be processed a second and a third time as needed to produce an AQP composition of suitable quality.

When AQP quality analyses are passed, the protein concentration was adjusted to 5 mg/ml by adding ice cold imidazole-free AQP binding buffer containing 2% LDAO. Finally, the AQP was sterilized by filtration through 0.45 μM sterilized cup and stored at 4° C. in refrigerator for use within a month or else stored at −80° C. in a freezer.

Preparation Method:
1. Prepare a fresh solution of Pluronic® P-123 by dissolving the polymer in PBS to a final concentration of 10 mg/mL in a glass cylinder.
2. Weight in a flask 15 mg/mL Jeffamine® M-2005.
3. Add Aquaporin Z stock solution to a final concentration of 1/200 AQPZ/polymer molar protein ratio, in which polymer is the combined amount of Pluronic® P-123 and Jeffamine M-2005.
4. Add Pluronic® P-123 solution prepared in step 1 to the mixture of
   Jeffamine® M-2005 and Aquaporin Z to reach 9.9 mg.
5. Stir the mixture overnight at 170 rotations per min (not more than 20 hours) at room temperature.
6. Next morning take the vesicle formulation obtained in the sequence of steps 1 to 5, transfer it to the storage flask and keep it at room temperature.

The vesicle formulation was tested for size, water permeability and zeta potential point of view by DLS, Zeta potential and stopped flow measurements in 0.5 M NaCl. The results are measured 5 times for 5 different batches.

TABLE 1

| Formulation | |
| --- | --- |
| Dh/nm (DLS) | 200 nm ± 24 (90% ± 10%) |
| | 28 nm ± 2 (0% ± 10%) |
| Zeta potential/mV | 3 ± 2 |
| Ki/s$^{-1}$ | 1702 ± 200 |

Temperature stability and thermal behavior were tested by warming up 5 mL of vesicle formulation for 10 min at various temperatures ranging from 30° C. to 100° C. and their size and water permeability was further determined by DLS and stopped-flow measurements.

Thermal treatment does not affect significantly the stability of the formulation, resulting in the diameter shrinkage of the larger size structures from around 200 nm at room temperature to around 1800 nm. From water permeability point of view no changes can be observed up to 100° C. Ki values from 1700 to 1687 s-1 were recorded.

The pH behavior shows the disassemble of vesicle formulation at pH varying from 1 to 7 to micelles with a diameter up to 20 nm and reassembling at basic pH values (from 9 to 13 showing the same size 180 nm and Ki values around 1700 s-1.

Example 2

Preparation of BWRO (Brackish Water Reverse Osmosis) Membranes

These membranes were made according to the steps outlined below:
a) Dissolve MPD in MilliQ water to get a 2.5% (W/W) concentration, see below
b) Dissolve TMC in Isopar to a final concentration of 0.15% W/V
c) Cover a rectangular shaped membrane, e.g. 5.5 cm×11 cm Membrana 1FPH PES membrane with about 20 mL/m2 membrane of MPD solution and leave for 30 seconds under gentle agitation
d) Dry the non-active side (back side) with lab drying paper (e.g. Kim-Wipe) for 5-10 seconds
e) Put the membrane on a glass plate and dry gently with N2 until the surface turns from shiny to dim
f) Apply tape around the edges of the membrane (≈1 mm)
g) Put the glass plate with the taped membrane into a glass or metal container, add about 155 mL/m2 membrane TMC-Isopar to one end and rock gently back and forth for 30 seconds
h) Remove glass plate from reservoir and dry with N2 for 10 to 15 seconds.

After removal of the tape the membrane can be transferred to MilliQ with the newly formed active side up and keep wet during handling in subsequent steps if necessary.

MPD solution calculation:

Weigh off 1.05 g of MPD and dissolve in 35 mL of MilliQ. Add 7 mL of liquid AQPZ composition prepared as described in example 1. Keep the solution topped with inert gas (Ar or N2) as much as possible.

TFC membranes with liquid AQPZ formulation of 5.5 cm×11 cm sizes was then be mounted in a Sterlitech CF042 FO cell (www.sterlitech.com) and subjected to tests of 60 minutes (5 membranes) and tests of 900 minutes (4 membranes) duration in FO mode using deionised (MilliQ) water as feed and 1 M NaCl aqueous solution as draw and feed and draw speeds of 268 mL/min.

Results are given in tables 4.

TABLE 4

Vesicle formulation tested on the RO low pressure membranes.

| Vesicle formulation | No. of Samples | Jw (L/m$^2$h) | Rejection NaCl (%) | Applied pressure, bar |
| --- | --- | --- | --- | --- |
| | 6 | 7.15 ± 0.5 | 90.5 ± 0.1 | 5 |

Example 3

Preparation of Handmade TFC FO (Forward Osmosis) Filtration Membranes

The membranes were made according to the steps outlined below:
a) Provide a support membrane, e.g. a PES non-woven having fingerlike structure, size 5.5 cm×11 cm
b) Mix 3 wt % MPD with 3 wt % ε-caprolactam, 0.5 wt % NMP, and 93.5 wt % DI water to obtain a solution
c) Add 0.1 mg/mL of liquid AQPZ formulation of example 1 to obtain a suspension
d) Incubate the suspension from c) for 2 hours
e) Prepare TMC solution from 0.09 wt % TMC, 0.9 wt % acetone, and 99.01 wt % Isopar
f) Dip coat the support membrane in the suspension d) for 30 seconds
g) Apply drying with air knife
h) Add the TMC solution from e) for interfacial polymerization
i) Follow with 2 min drying in fume hood Three membranes were made and mounted in a Sterlitech CF042 RO cell, www.sterlitech.com, operated at 5 bar using 500 ppm NaCl as feed for 60 minutes.
Results are given in table 5.

TABLE 5

Vesicle formulation tested on the FO handmade membranes

| Vesicle formulation | No. of Samples | Jw (L/m²h) | Js (gmh) | Js/Jw |
|---|---|---|---|---|
| | 3 | 10.84 ± 1.2 | 2.03 ± 0.2 | 0.18 ± 0.1 |

Example 4

Preparation of FO (Forward Osmosis) Membranes

Vesicles incorporating AqpZ were prepared by firstly mixing the aqueous solution of transmembrane protein (Aquaporin Z stock solution as prepared above) with polyetheramine (15 mg/mL Jeffamine® M-2005) to obtain a final concentration of 1/200 AQPZ/polymer molar protein ratio. Subsequently, adding PEO-PPO-PEO aqueous solution (Pluronic® P-123 having a molecular weight of 5800 Da in PBS to a final concentration of 10 mg/mL), and agitating the mixture overnight at 170 rotations per min at room temperature.

Such prepared vesicles were incorporated into the polyamide thin-film composite (TFC) membrane, by interfacial polymerization on the porous support. Aqueous solution was prepared comprising the vesicle mixture (6 ml of the mixture prepared above) and m-phenylenediamine solution (prepared by dissolving 1.5 g MPD in 52.5 ml MilliQ). The organic solution
comprised of trimesoyl chloride (TMC) and Isopar™ E in a concentration of 0.15% W/V.

As detailed above, the coating protocol comprised soaking the porous support with aqueous solution, followed by gentle removal of its excess. Subsequently, organic solution was applied and polyamide layer was formed, excess of organic solution was gently dried. The membranes were stored in miliQ water prior testing.

Vesicle properties: Ki $1412 s^{-1}$, pH 9.83, Zeta potential −0.339 (average), size: 204 nm (average), 100% population. The dimensions of the extruded vesicles (hydrodynamic diameter) were determined by dynamic light scattering using ZetaSizer NanoZs from Malvern. The water flux through AQP channels was tested using a Bio-Logic SFM 300 stopped-flow device, using a monochromator at 517 nm and a cut off filter at 530 nm. For each individual stopped-flow test, 0.13 ml extruded polymersome or AQP inserting polymersomes was quickly mixed with 0.13 ml NaCl 0.5 M, which caused water efflux from vesicles that resulted in vesicle shrinkage. The kinetic data were fitted with a double exponential equation, and the rate constant $(s^{-1})$ that is directly proportional with the water flux through polymeric membrane was determined.

The test was made on the Forward Osmosis setup with 1 M salt as the draw solution and 5 µM calcein as feed. The draw and feed solution were pumped counter-currently, with the active side of the membrane facing feed solution. The results are presented in table 6 below.

TABLE 6

| Vesicles incorp. | Jv | Js | Calcein R | Js/Jv |
|---|---|---|---|---|
| Yes | 11.17 ± 1.61 | 1.23 ± 0.25 | 99.80 ± 0.14 | 0.14 ± 0.02 |
| No | 4.85 ± 1.02 | 0.82 ± 0.74 | 99.85 ± 0.02 | 0.15 ± 0.10 |
| Commercially available | >10 | <3 | >99% | <0.3 |

Membranes containing amino modified vesicles incorporating AqpZ protein, resulted in improved performance when compared to the membranes without the vesicles. The average water flux through the membrane $(J_v)$ was improved by 84% ($J_v$=11.17±1.61 $Lm^{-2}h^{-1}$ vs $J_v$=4.85±1.02 $Lm^{-2}h^{-1}$), while rejection of calcein (R) stayed on the comparable level (R>99%). Reverse salt flux increased on average by 50% when incorporating vesicles ($J_s$=1.23±0.25 $gm^{-2}h^{-1}$ vs $J_s$=0.82±0.74 $gm^{-2}h^{-1}$), nevertheless the overall performance by means of specific salt flux $J_s/J_v$ stayed on comparable level (0.14±0.02 for membrane with vesicles, compared to 0.15±0.10 for membrane without vesicles).

The data show that amino decorated vesicles incorporating aquaporin proteins are an efficient way to incorporate AqpZ protein into the polyamide membranes, resulting in improvement of the water flux, without compromising the specific salt flux. Without wishing to be bound by any particular theory, it can be explained that vesicles containing amine groups on the surface will be not only physically incorporated, but, in addition chemically bound in the polyamide layer of the TFC membrane, because of the presence of the reactive amine groups. These amine groups will participate in the interfacial polymerization reaction with acyl chloride to obtain vesicles being covalently bound to the layer. The covalent bonding opens the possibility for higher vesicle loading and thus higher water flux through the membranes.

Example 5

Vacuum-Mediated Coating

The porous support was mounted in a suction cell with the active layer facing upwards, and a vacuum pump applied underneath, facing the inactive layer. The support for used for the TFC layer was MicroPES 1F PH microporous support from Membrana GmbH. 50 mL of aqueous solution containing MPD and Formulation 10-2-10 in RO water was poured into the suction cell, covering the porous support. Afterwards, a suction of 100 mBar was applied for 5 minutes, sucking the MPD and formulation onto the support.

Vacuum was turned off and 50 mL of organic solution containing TMC and Isopar-E was applied and given 1 minute of reaction time to facilitate the interfacial polymerization. The organic solution was then flushed out, and the membrane was left to dry for 3 minutes and was then transferred to a petri dish with RO water until ready for QC testing.

Formulation 10-2-10: 10 mg/ml Pluronic f127 (poloxamer 407)-2 mg/ml Jeffamine M2005-10 mg/ml aquaporin stock solution. in PBS buffer (137 mM NaCl, 2.7 mM KCl, 10 mM $Na_2HPO_4$ and 2 mM of $KH_2PO_4$).

TABLE 7

Quality testing of forward osmosis membranes by vacuum-mediated coating

| Formulation | Series 1 | Series 2 | Series 3 | Average and std |
|---|---|---|---|---|
| Control - aqueous solution w/o formulation | Jw: 1.45<br>Js: 311.02<br>100% | Jw: 2.40<br>Js: 262.98<br>99.69% | —<br>—<br>— | Jw: 1.92 ± 0.5<br>Js: 287 ± 24<br>99.9% ± 0.2 |
| 2% v/v formulation | Jw: 2.72<br>Js: 1.39<br>99.93% | Jw: 2.32<br>Js: 0.48<br>99.75% | Jw: 2.00<br>Js: 3.48<br>99.89% | Jw: 2.35 ± 0.3<br>Js: 1.78 ± 1.3<br>99.9% ± 0.1 |
| 5% v/v formulation | Jw: 1.69<br>Js: 0.50<br>99.95% | Jw: 1.64<br>Js: 0.34<br>99.51% | Jw: 1.99<br>Js: 1.08<br>99.87% | Jw: 1.77 ± 0.2<br>Js: 0.64 ± 0.3<br>99.8% ± 0.2 |
| 7% v/v formulation | Jw: 1.38<br>Js: 0.86<br>99.76% | Jw: 1.44<br>Js: 0.40<br>99.56% | Jw: 1.79<br>Js: 0.81<br>99.64% | Jw: 1.54 ± 0.2<br>Js: 0.69 ± 0.2<br>99.7% ± 0.1 |
| 10% v/v formulation | Jw: 1.98<br>Js: 1.61<br>99.82% | Jw: 1.37<br>Js: 0.83<br>99.96% | Jw: 2.46<br>Js: 2.09<br>99.99% | Jw: 1.94 ± 0.4<br>Js: 1.51 ± 0.5<br>99.9% ± 0.1 |

Results of Quality testing of Forward Osmosis membranes prepared by vacuum-mediated coating
Flux, here denoted as Jw, is measured in L/m^2 h
Salt flux, here denoted as Js, is measured in g/m^2 h
Calcein rejection is measured in %

While the water flux and the calcein rejection did not differ substantially from the control coupons, the salt flux was significantly lower in the coupons coated with solutions containing formulation as opposed to controls coated with a TFC layer without formulation. This indicates that the presence of the formulation decreased the salt flux (and thus increased salt rejection). A student's unpaired t-test showed a strong trend when comparing salt flux of control membranes with formulations, with p-values ranging from 0.053191 (2%) to 0.053386 (10%). It did not seem that an increase in percentage wise concentration of formulation in the aqueous solution used for coating influenced the level of salt rejection.

Example 6

Amino Decorated Vesicle Incorporating Transmembrane Protein

Preparation method of vesicles that incorporate Aquaporin Z:
1. Prepare a fresh solution of Pluronic® P-123 by dissolving the polymer in PBS to a final concentration of 10 mg/mL in a glass cylinder.
2. Weight in a flask 15 mg/mL Jeffamine® M-2005.
3. Add Aquaporin Z stock solution to Jeffamine® M-2005 bottle, to obtain a final concentration of 1/200 AQPZ/P-123-Jeffamine molar protein ratio.
4. Add Pluronic® P-123 solution prepared in step 1 to the mixture of Jeffamine® M-2005 and Aquaporin Z to reach 9.9 mg/mL.
5. Stir the mixture overnight at 170 rotations per min (not more than 20 hours) at room temperature.
6. Next morning take the vesicle formulation obtained in the sequence of steps 1 to 5, transfer it to the storage flask and keep it at room temperature.

Preparation method of control vesicles which does not incorporate Aquaporin Z:
1. Prepare a fresh solution of Pluronic® P-123 by dissolving the polymer in PBS to a final concentration of 10 mg/mL in a glass cylinder.
2. Weight in a flask 15 mg/mL Jeffamine® M-2005.
3. Add Pluronic® P-123 solution prepared in step 1 to the mixture of Jeffamine® M-2005 to reach 9.9 mg/mL.
4. Stir the mixture overnight at 170 rotations per min (not more than 20 hours) at room temperature.
5. Next morning take the vesicle formulation obtained in the sequence of steps 1 to 5, transfer it to the storage flask and keep it at room temperature.

The vesicle formulations were both tested for size, water permeability and zeta potential point of view by DLS, Zeta potential and stopped flow measurements in 0.5 M NaCl.

Characterization of vesicles:
The dimensions of the vesicles (hydrodynamic diameter) are determined by dynamic light scattering using ZetaSizer Nano ZS from Malvern. The water flux through vesicle membrane is tested using a Bio-Logic SFM 300 stopped-flow (SF) device, using a monochromator at 517 nm and a cut-off filter at 530 nm. For each individual SF test, 0.13 ml polymersomes or AqpZ embedding polymersomes samples, were quickly mixed with 0.13 ml NaCl 0.5 M, which caused water efflux from vesicles resulting in vesicle shrinkage.

TABLE 8

| Formulation | Hydrodynamic diameter (nm) - % Intensity | | Zeta potential (mV) | pH | Osmotic coefficient $k_i$ ($s^{-1}$) |
| | Population 1. | Population 2. | | | |
|---|---|---|---|---|---|
| Pluronic ® vesicles reconstituting Aquaporin Z | 158 ± 63 – 93% | 34 ± 8 – 7% | +3 | 9.91 | 1700 |
| Pluronic ® vesicles without Aquaporin Z | 147 ± 49 – 95% | 33 ± 6 – 5% | +3 | 9.92 | 200 |

Table 8 shows the osmotic coefficient k, which is calculated based the exponential growth of the stopped-flow light scattering results for the vesicles incorporating Aquaporin Z and blank ones. The analysis of exponential growth is made on the first population of the structures showing the most rapid shrinkage. The osmotic coefficient k ($s^{-1}$) is directly proportional with the water flux through polymeric membrane and the results show that the presence of aquaporins in the vesicles significantly increases the water flux through polymeric membrane. The other properties of the vesicles are substantially unaffected by the presence of aquaporin Z, i.e. the hydrodynamic diameter, zeta potential and the pH remain at the same level.

Example 7

Preparation Method of TFC FO Membranes Incorporating Vesicles Reconstituting Aquaporin Z:
a) Provide a support membrane, e.g. PES non-woven having fingerlike structure, size 5.5 cm×11 cm.
b) Prepare MPD solution in MiliQ water, to obtain 2.5% (W/W) concentration. If Aquaporins are to be incorporated to the membrane, add the solution of vesicles. The final concentration of MPD solution can contain from 10 g/L to 100 g/L solution of vesicles.
c) Prepare TMC solution in Isopar E, to obtain 0.15% (W/V)
d) Soak rectangle shaped membrane in MPD solution to completely cover the membrane surface
e) Transfer rectangle shaped membrane from MPD solution to dry the side which will be non-active side on the lab drying paper (e.g. Kim-Wipe) for 5-10 seconds
f) Put the membrane on a glass plate and dry gently with N2 until the surface turns from shiny to dim
g) Apply tape around the edges of the membrane (≈1 mm)
h) Transfer a glass plate with the taped membrane into a glass container and cover the membrane with TMC solution, to completely cover the membrane surface
i) Remove the glass plate from reservoir and dry with N2 until the surface turns shiny to dim
j) Put the membrane on a glass plate in horizontal position for about 10 seconds, and remove the tape
k) Transfer the membrane to the first container filled with MilliQ for 5 minutes
l) Transfer the membrane to the second to the container filled with MilliQ for storage, prior testing described in subsequent steps.

Testing of TFC FO Membranes

TFC FO membranes with Aquaporin Z formulation of 5.5 cm×11 cm sizes were then mounted in a Sterlitech CF042 FO cell (www.sterlitech.com) and subjected to tests of 200 minutes duration in FO mode, using 5 µM calcein in deionised (MilliQ) water as feed and 1 M NaCl aqueous solution as draw and feed and draw speeds of 50 mL/min.

TABLE 9

| Membrane number in batch | Vesicles | Jv calculated [$Lm^{-2}h^{-1}$] | Js calculated [$gm^{-2}h^{-1}$] | Calcein rejection [%] | Js/Jv [$gL^{-1}$] |
|---|---|---|---|---|---|
| 1 | 1% of vesicles | 11.17 | 1.45 | 99.88 | 0.13 |
| 2 | incorporating | 7.79 | 1.32 | 99.78 | 0.17 |
| 3 | Aquaporin Z | 9.04 | 1.27 | 99.61 | 0.14 |
| 4 | | 7.73 | 0.87 | 99.91 | 0.11 |

TABLE 9-continued

| Membrane number in batch | Vesicles | Jv calculated [$Lm^{-2}h^{-1}$] | Js calculated [$gm^{-2}h^{-1}$] | Calcein rejection [%] | Js/Jv [$gL^{-1}$] |
|---|---|---|---|---|---|
| 1 | Without | 3.90 | 0.32 | 99.84 | 0.08 |
| 2 | vesicles | 5.01 | 0.59 | 99.84 | 0.12 |
| 3 | | 6.21 | 1.91 | 99.86 | 0.31 |
| 4 | | 4.27 | 0.44 | 99.87 | 0.10 |

Table 9 shows the results of FO experiment with membranes incorporating vesicles incorporating Aquaporin Z proteins and comparison to the blank ones (control membranes). It may be concluded that Jv increases by the incorporation of the vesicles incorporating Aquaporin Z and that the Js/Jv remains at the same level.

The invention claimed is:
1. A vesicle incorporating a transmembrane protein, wherein the vesicle forming material comprises a mixture of poly(ethylene glycol)-block-poly(propylene glycol)-block-poly-(ethylene glycol) and polyetheramine.
2. The vesicle according to claim 1, wherein the poly (ethylene glycol)-block-poly(propylene glycol)-block-poly (ethylene glycol) is a substantially linear polymer having an average molecular weight of between about 1,000 Da to about 15,000 Da.
3. The vesicle according to claim 1, wherein the poly (ethylene glycol)-block-poly(propylene glycol)-block-poly (ethylene glycol) has the chemical formula:

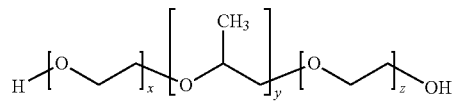

in which
x denotes an integer between 10-30,
y denotes an integer between 50-100, and
z denotes an integer between 10-30.
4. The vesicle according to claim 1, wherein the polyetheramine is of the general structure

in which
m is an integer of 1-15,
n is an integer of 5-50, and
R=$CH_3$.
5. The vesicle according to claim 1, wherein the proportion by weight between the poly(ethylene glycol)-block-poly(propylene glycol)-block-poly(ethylene glycol) and the polyetheramine is 5 to 1.
6. The vesicle according to claim 1, wherein the transmembrane protein is an aquaporin water channel.
7. A method of preparing vesicles incorporating a transmembrane protein comprising:
a. mixing an aqueous solution of transmembrane protein and polyetheramine,
b. adding poly(ethylene glycol)-block-poly(propylene glycol)-block-poly(ethylene glycol) as an aqueous solution to the mixture prepared step a,
c. agitating the solution obtained in step b.

8. The method according to claim 7, wherein the poly(ethylene glycol)-block-poly(propylene glycol)-block-poly(ethylene glycol) is a substantially linear polymer having an average molecular weight of between about 1,000 Da to about 15,000 Da.

9. The method according to claim 7, wherein the poly(ethylene glycol)-block-poly(propylene glycol)-block-poly(ethylene glycol) has the chemical formula:

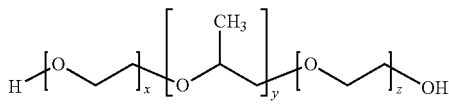

in which
x denotes an integer between 10-30,
y denotes an integer between 50-100, and
z denotes an integer between 10-30.

10. The method according to claim 7, wherein the polyetheramine is of the general structure

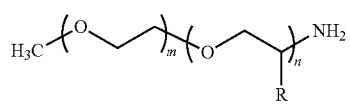

in which
m is an integer of 1-15,
n is an integer of 5-50, and
R=CH$_3$.

11. The method according to claim 7, wherein the proportion by weight between the poly(ethylene glycol)-block-poly(propylene glycol)-block-poly(ethylene glycol) and the polyetheramine is 5 to 1.

12. The method according to claim 7, wherein the transmembrane protein is an aquaporin water channel.

13. A separation membrane comprising a vesicle incorporating a transmembrane protein, wherein the vesicle forming material comprises a mixture of poly(ethylene glycol)-block-poly(propylene glycol)-block-poly(ethylene glycol) and polyetheramine.

14. The separation membrane according to claim 13, comprising an active layer incorporating the vesicle and a porous support membrane, said active layer comprising the vesicle incorporated in a thin film composite layer formed on the porous substrate membrane.

15. The separation membrane according to claim 13, having the form of a hollow fiber.

16. The separation membrane according to claim 15, wherein a bundle of hollow fibers is assembled in a housing to form a hollow fiber module, said hollow fiber module comprising an inlet connected to at least one lumen of a hollow fibers in one end for passing a first solution and an outlet connected to said at least one lumen in the other end, and an inlet provided in the housing for passing a second solution to an outlet connected to the housing.

17. The separation membrane according to claim 13, having the form of a flat sheet.

18. The separation membrane according to claim 17, wherein the separation membrane is spiral wound for the formation of a spiral wound membrane module.

19. The separation membrane according to claim 13, wherein the poly(ethylene glycol)-block-poly(propylene glycol)-block-poly(ethylene glycol) has the chemical formula:

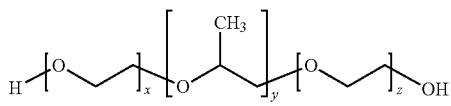

in which
x denotes an integer between 10-30,
y denotes an integer between 50-100, and
z denotes an integer between 10-30.

20. The separation membrane according to claim 13, wherein the polyetheramine is of the general structure

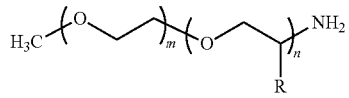

in which
m is an integer of 1-15,
n is an integer of 5-50, and
R=CH$_3$.

* * * * *